United States Patent [19]

Junker

[11] Patent Number: 5,167,236
[45] Date of Patent: Dec. 1, 1992

[54] TINNITUS-MASKER

[76] Inventor: Franz Junker, Entengasse 10, 7505 Ettlingen, Fed. Rep. of Germany

[21] Appl. No.: 690,881
[22] PCT Filed: Dec. 15, 1989
[86] PCT No.: PCT/DE89/00776
    § 371 Date: Jun. 6, 1991
    § 102(e) Date: Jun. 6, 1991
[87] PCT Pub. No.: WO90/07251
    PCT Pub. Date: Jun. 28, 1990

[30] Foreign Application Priority Data

Dec. 22, 1988 [DE] Fed. Rep. of Germany ... 8815877[U]

[51] Int. Cl.$^5$ .............................................. A61B 5/00
[52] U.S. Cl. ..................................... 128/746; 128/789
[58] Field of Search ............... 128/746, 789, 784, 783; 604/36; 600/28

[56] References Cited

U.S. PATENT DOCUMENTS 4,222,393 9/1980 Hocks et al. .......................... 128/746
4,759,070 7/1988 Voroba et al. ....................... 128/746

FOREIGN PATENT DOCUMENTS 2134689 8/1984 United Kingdom .

Primary Examiner—Max Hindenburg
Attorney, Agent, or Firm—Sprung Horn Kramer & Woods

[57] ABSTRACT

A tinnitus masker having an electric circuit arranged in a housing and an earpiece which produces a sound spectrum that masks the trinitus is disclosed. The electronic circuit is designed so that the sound spectrum produced by the earpiece contains a line spectrum with a fundamental tone.

11 Claims, 2 Drawing Sheets

TINNITUS-MASKER

This invention refers to a tinnitus-masker with an electronic circuit arranged in a housing, an earphone to produce a spectrum of sound in order to mask the tinnitus of the patient and with a volume control to adjust the sound intensity.

Tinnitus defines a disease in which the patient notices noise in his ears or his head for which no external sources can be traced. This can be extremely annoying and possibly leads in difficult cases to severe psychic and physiological symptoms.

Scientific literature shows, that since many years research efforts have been made to cure tinnitus disease by masking the tinnitus noise by means of sound signals lead to the ears. Numerous investigations have been carried out by M. Feldmann, who tested the influence of wide band noises, small band noises and pure tones. The following publications are to be pointed out:

H. Feldmann: "Homolaterale und kontralaterale Verdeckung von subjektiven Ohrgeräuschen durch Breitbandgeräusche, Schmalbandgeräusche und reine Töne"; Arch. klin. exp. Ohr.-Nas.-Kehlk.-Heilk. 194, 460–465 (1969).

H. Feldmann: "Homolateral and contralateral masking of tinnitus by noise—bands and pure tones"; Audiology, 10, 138-144 (1971).

H. Feldmann: "Homolateral and contralateral masking of tinnitus, Proceedings of the 1st International Tinnitus Seminar"; J. Laryngol. Otol. Suppl. 4, S.60-70 (1981).

In order to provide patients with a means to ease the problems of their disease, even outside of their homes and independently of big and complicated appliances, miniaturized tinnitus - maskers have recently been made available. These are either individual appliances or they are integrated into hearing aids. Another proposal is a signal transmitter which can be fixed to a conventional hearing aid (DE-A-3027791).

In case of these appliances, special care is taken that the masking noise has a wider bandwidth than the noise in the ears it is supposed to mask (R. Schönweiler: "Ohrgeräusche: Ursachen, Bewertung und Therapie"; Dtsch. med. Wschr. 111, 1489–1494, insbesondere 1492 linke Spalte, (1986)). Known tinnitus maskers therefore use a noise signal which has a wide, indifferent frequency spectrum, extending over the whole audible spectrum of sound, normally possessing a wide maximum between approximately 1000 Hz and 5000 Hz. The exact profile of the sound spectrum is defined by the individual supplier of the appliance. Generally the patient can only regulate the volume by means of a respective control knob. Only a few appliances provide the possibility to influence frequency response through sound control. The effect of these sound controls is to either preemphasize or lower certain parts of the frequency spectrum (especially deeper tones).

From SE-B-428 860 and GB-A-2 134 689 tinnitus-maskers are known in which the frequency spectrum of the masking sound can be modified to a major degree. To this end SE-B 428 860 discloses a programming unit which is separable from the signal generating unit and which serves for inputing information with respect to the desired noise spectrum. This information is transferred from case to case (batchwise) to a memory integrated into the signal generation unit. This allows generation of relatively complicated noise spectra in accordance with the information stored in the memory. Direct adjustment by the patient himself is not possible. Furthermore the device requires a high expenditure in electronics. Digital programming is also used in the system of GB-A 2 134 689. Here a separate characterizing system is required. A specialist is supposed to determine the noise spectrum suited for an individual patient by means of this characterizing system. The masker is programmed accordingly. Again this digital operating system requires a high design expenditure. No adjustment by the patient himself is possible.

The invention is directed to providing a tinnitus-masker with improved efficiency. Simultaneously the expenditure for electronics should be as limited as possible to allow optimal miniaturization.

This is achieved by a tinnitus-masker as specified at the outset in which the electronic circuit is so designed, that the spectrum of noise, produced by the earphone, contains a line spectrum with one fundamental tone wherein the frequency of the fundamental tone can be adjusted by the user.

Surprisingly it was found, that with many tinnitus patients good results were achieved by means of simple harmonic oscillation, adjustable by the user himself both with respect to intensity and frequency of fundamental tone. Patients adjust frequency and volume according to their different requirements. It was found that some patients at different times needed quite different frequencies for optimal effect. Occasionally even those frequencies turned out to be effective which are out of the normal audible range. Therefore the frequency is preferably adjustable between 0,125 kHz and 20 kHz. The invention comprises, however, also less sophisticated embodiments with an adjustment range ranging only from 3000 to 8000 Hz, preferably from 1 kHz to 12 kHz. In any case the upper limit of the frequency setting range should differ from the lower limit by at least a factor of 2, preferably a factor of 4.

Good results can be obtained either through harmonic oscillation (sinusoidal oscillation) or nonharmonic periodic oscillation and here especially square waves, both with variable frequency.

According to an especially preferred embodiment the tinnitus-masker is provided with a switch operable by the user to enable him, to (preferably alternatively) connect different periodic oscillations (each with variable frequency) to the earphone.

In the following the invention will be further illustrated by means of an embodiment shown schematically in the attached drawings in which FIG. 1 shows a tinnitus-masker according to the invention in perspective view.

Figure 1:
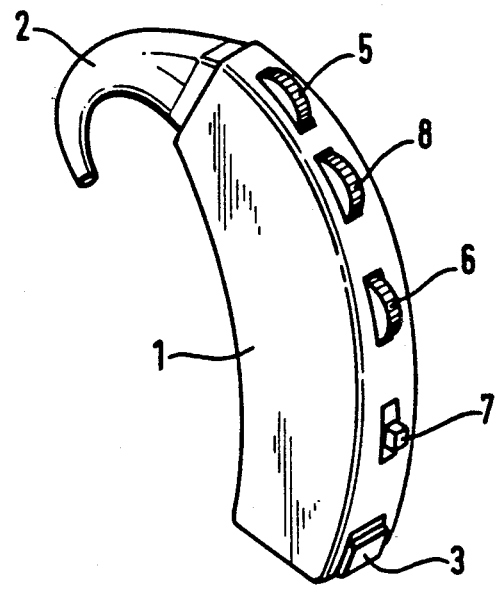

The tinnitus-masker shown in FIG. 1 has a housing 1 and a connectable hearing channel 2 similar to hearing aids that are carried behind the ear. The hearing channel 2 is connected with the patient's ear via a specially adapted telephone olive which is commonly used with hearing aids (not shown in FIG. 1). As usual housing 1 comprises a battery box 3.

Adjusting knob 5 is used to adjust the intensity of the sound. A further adjusting knob 6 is provided to adjust the frequency of the fundamental tone. Alternation switch 7 is used for the change- over between two different periodic oscillations, especially between sinus and rectangular. Adjusting knob 8 is provided to adjust the intensity of an admixable (superposed) noise signal.

Figure 2:
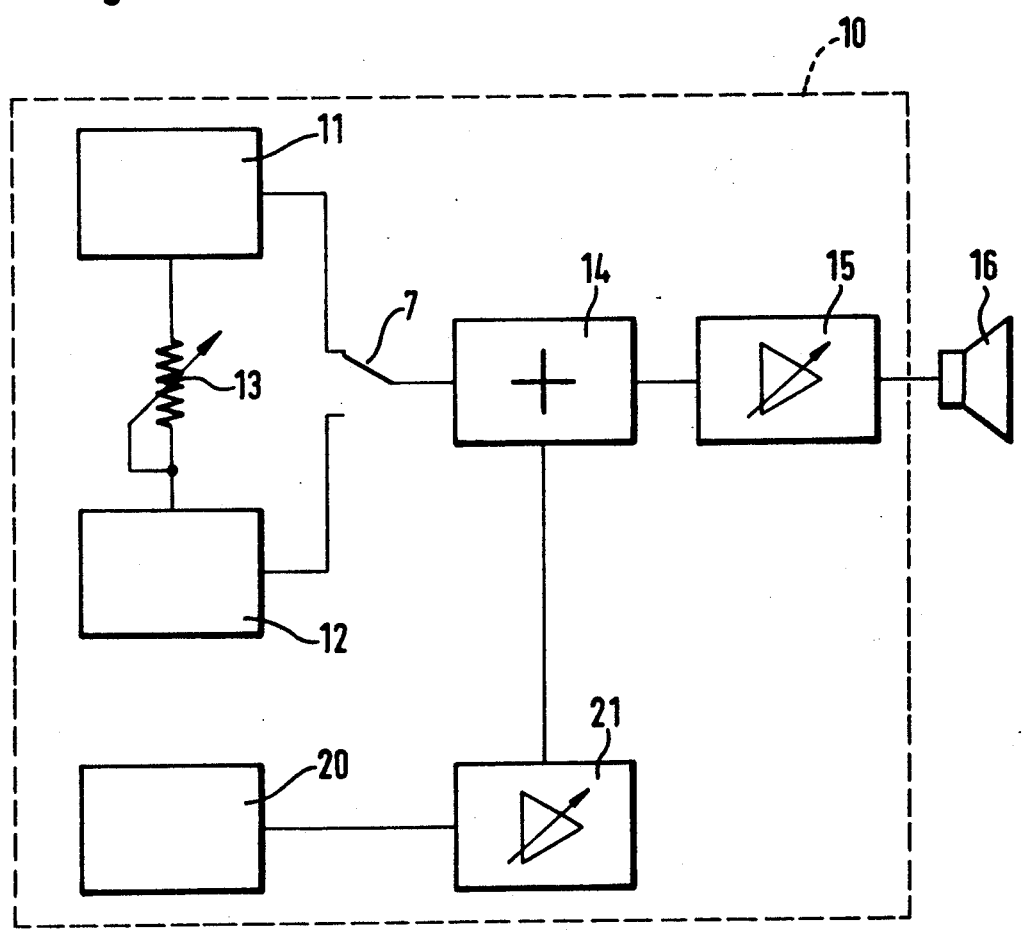
FIG. 2 shows a block diagram of an electronic circuit suitable for a tinnitus-masker according to the invention.

FIG. 2 shows a circuit 10, comprising a sine wave generator 11, a square wave generator 12, and a potentiometer 13, which is used as frequency controller and operated by adjusting knob 6. Adjusting knob 7 and adding device 14 feed alternatively sine wave signals of generator 11 or square wave signals of generator 12 to variable gain amplifier 15. The amplification factor can be controlled by means of adjusting knob 5. The output signal of amplifier 15 is connected to earphone 16 which produces a sound signal which is led to hearing channel 2.

According to a preferred embodiment there is provided an additional noise generator 20, which is connected via variable gain amplifier 21 to adding device 14. The signal is combined with the periodic signals of sine wave generator 11 or square wave generator 12. The amplification factor of amplifier 21 (that means, more generally speaking, the intensity of the admixed noise signal) is adjustable through adjusting knob 8, preferably through the user himself. In this embodiment, the intensity of the noise signal should always be lower than the intensity of the periodic signal.

The design of the individual circuit elements shown in FIG. 2 is not described in detail, since a person skilled in the electronic art has readily available knowledge about different realisation possibilities for signal generators, adders, and amplifiers, from technical literature which is available. Also readily available on the market are integrated circuit elements. The electronic circuitry has a very simple design. This allows miniaturisation into a very small housing.

The FIGS. 3 to 6 show four different sound signal spectra of a tinnitus-masker according to the invention. In each case the frequency lays off as abscissa and the amplitude as ordinate. The respective frequencies of the spectral lines and of the right hand limit of the frequency range are indicated.

Figure 3:
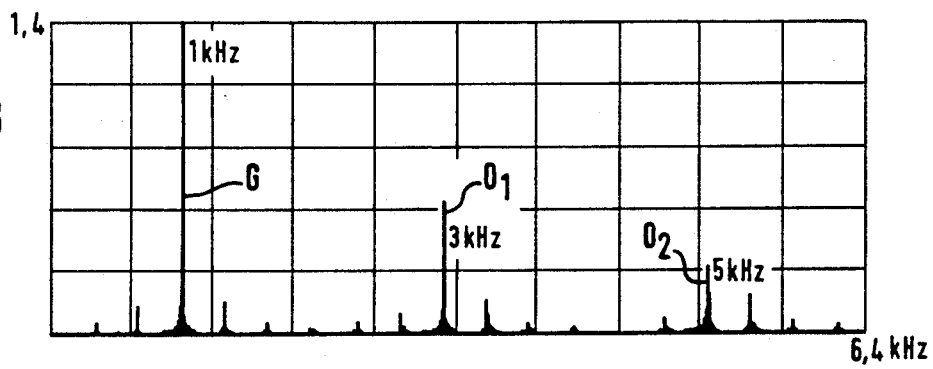
FIG. 3–FIG. 6 show graphical representations of four different spectra of a tinnitus-masker according to the invention.

FIG. 3 shows the line spectrum of a 1 kHz square wave signal. The fundamental tone line G at 1 kHz has the highest amplitude. Overtone lines $O_1$ and $O_2$ are indentified at 3 kHz and 5 kHz. Further frequency lines with lower amplitudes are caused by the fact that the electronic circuit used can not produce an ideal rectangle. Within the context of this invention this is tolerable as long as the sound spectrum contains a clearly defined line spectrum and as long as it is possible for the user to adjust the fundamental tone line in a wide frequency range, as described before.

Figure 4:
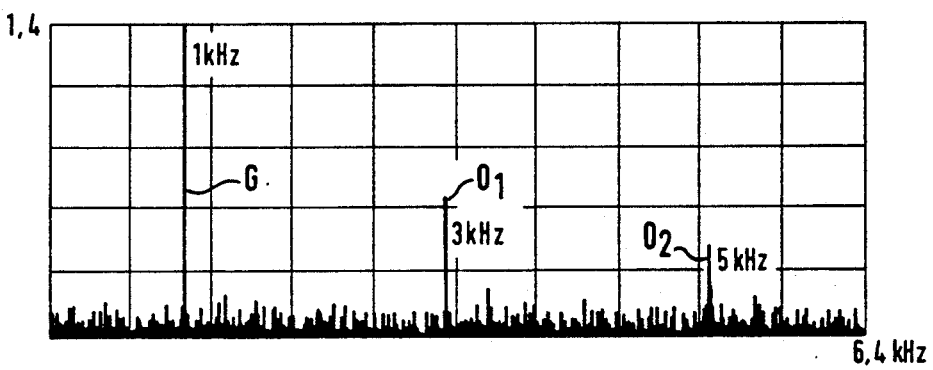

As mentioned above, it can be advantageous to admix a noise spectrum with comparatively lower amplitude to the line spectrum,. This is shown in FIG. 4 in which the 1 kHz square wave spectrum shown in FIG. 3 is superposed by a noise signal, the amplitude of which is substantially lower than the frequency line of the second overtone $O_2$. In any case it is necessary that the noise spectrum shows a substantially lower average amplitude compared to the fundamental tone line (preferably less than 50%, more preferably less than 20%).

Figure 5:
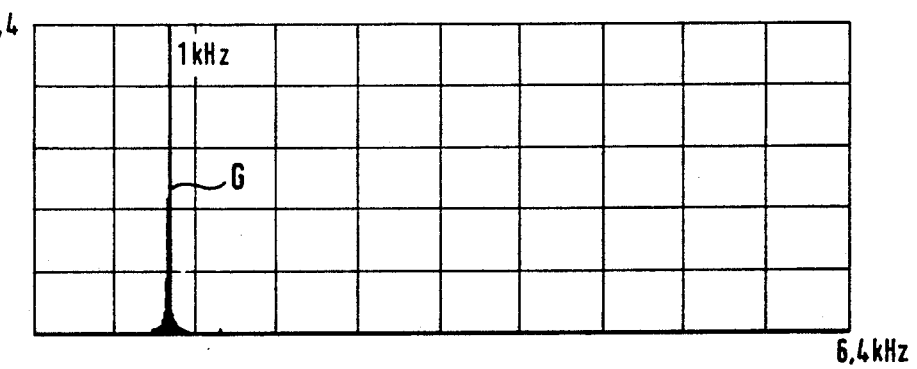
Figure 6:
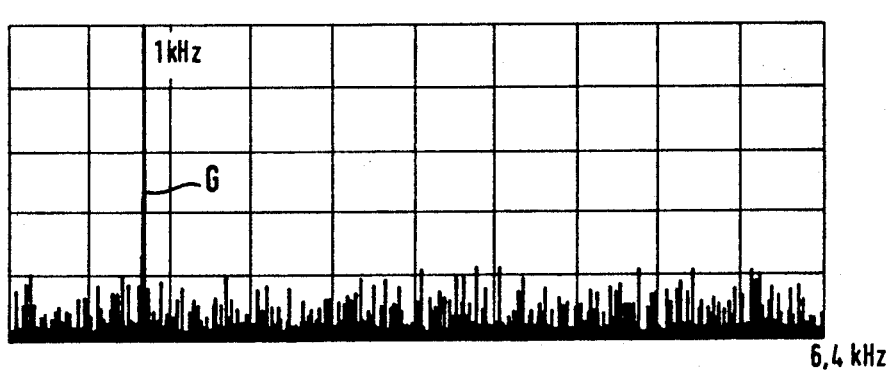

FIG. 5 and FIG. 6 are representations analogous to FIG. 3 and 4, but showing a case, where the line spectrum is based on a harmonic oscillation (sinusoidal signal). In FIG. 5 the spectrum is dominated by the line of the 1 kHz fundamental oscillation. FIG. 6 shows an additional superposed noise signal, the amplitude of which is in average less than 20% of the amplitude of the fundamental tone.

I claim:

1. A tinnitus-masker wearable by a patient during use and comprising:
   an earphone responsive to electrical signals for producing sounds; and
   electronic circuit means connected to the earphone for producing electrical signals to effect the generation of a spectrum of sound comprising a line spectrum with a fundamental tone for masking the tinnitus of a patient during use;
   wherein the electronic circuit means has means controllable by the patient during use of the masker for adjusting the intensity of sound generated by the earphone and means controllable by the patient during use of the masker for adjusting the fundamental tone of the sound generated by the earphone.

2. The tinnitus-masker according to claim 1, wherein the frequency of the fundamental tone is adjustable between 0.125 and 20 kHz.

3. The tinnitus-masker according to claim 1, wherein the electronic circuit means further comprises means for generating a sinusoidal oscillation signal and applying same to the earphone.

4. The tinnitus-masker according to claim 3, wherein the electronic circuit means further comprises means for generating a nonharmonic periodic oscillation signal and means for applying same to the earphone.

5. The tinnitus-masker according to claim 4, wherein the means for applying the oscillation signals to the earphone comprises a switch actuatable by the patient during use of the masker for selecting between the sinusoidal and nonharmonic periodic oscillation signals.

6. The tinnitus-masker according to claim 4 or 5, wherein the nonharmonic periodic oscillation signal is a square wave signal.

7. The tinnitus-masker according to claim 1, wherein the electronic circuit means further comprises means for generating a nonharmonic periodic oscillation signal and means for applying same to the earphone.

8. The tinnitus-masker according to claim 1, wherein the electronic circuit means further comprises means for generating a noise signal, and for superposing same on the line spectrum.

9. The tinnitus-masker according to claim 8, further comprising means controllable by the patient during use of the masker for adjusting the intensity of the noise signal.

10. The tinnitus-masker according to claim 1, wherein the upper limit of the adjustable range of the fundamental tone frequency differs from the lower limit of the adjustable range of the fundamental tone frequency by at least a factor of 2.

11. The tinnitus-masker according to claim 1, wherein the upper limit of the adjustable range of the fundamental tone frequency differs from the lower limit of the adjustable range of the fundamental tone frequency by at least a factor of 4.

* * * * *